United States Patent
Bays et al.

(10) Patent No.: US 6,222,070 B1
(45) Date of Patent: Apr. 24, 2001

(54) METHOD FOR REDUCING EDA IN ACETIC ANHYDRIDE PRODUCTION

(75) Inventors: Joseph Nathaniel Bays; Joseph Robert Zoeller; Michael Roy Cushman; Brent Alan Tennant, all of Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/390,834

(22) Filed: Sep. 7, 1999

(51) Int. Cl.$^7$ ............................. C07C 51/54; B01J 38/58
(52) U.S. Cl. ..................... 562/891; 562/888; 562/889; 562/890; 562/893; 502/30; 502/53
(58) Field of Search ..................... 562/891, 893, 562/888, 889, 890; 502/30, 53

(56) References Cited

U.S. PATENT DOCUMENTS

| 4,046,807 | 9/1977 | Kuckertz . |
| 4,252,741 | 2/1981 | Porcelli et al. . |
| 4,374,070 | 2/1983 | Larkins et al. . |
| 4,430,273 | 2/1984 | Erpenbach et al. . |
| 4,559,183 | 12/1985 | Hewlett . |
| 4,661,631 | 4/1987 | Becker et al. . |
| 4,735,749 | 4/1988 | Jujiwa et al. . |
| 4,994,608 | 2/1991 | Torrence et al. . |
| 5,237,097 | 8/1993 | Smith et al. . |
| 5,922,911 | 7/1999 | Jones et al. . |

FOREIGN PATENT DOCUMENTS

| 0 087 870 A1 | 9/1983 | (EP) . |
| 6-40998 | 2/1994 | (JP) . |

*Primary Examiner*—Paul J. Killos
*Assistant Examiner*—Robert W. Deemie
(74) *Attorney, Agent, or Firm*—Matthew Smith; Harry Gwinnell

(57) ABSTRACT

In a liquid phase carbonylation process for the production of acetic anhydride by reacting a feed stream which includes methyl acetate, methanol and carbon monoxide using a Group VIII metal-containing catalyst, and preferably a rhodium containing material, a liquid reaction product is continuously withdrawn from the carbonylation zone and fed to an evaporation/separation zone for separating volatile constituents of the reaction from the non-volatile constituents which, includes a portion of the Group VIII metal catalyst from the carbonylation reactor. The Group VIII metal catalyst is contacted with a gas stream which includes hydrogen for a period of from about 0.001 seconds to about 200 seconds as it is being returned to the carbonylation zone.

23 Claims, No Drawings

US 6,222,070 B1

METHOD FOR REDUCING EDA IN ACETIC ANHYDRIDE PRODUCTION

BACKGROUND OF THE INVENTION

1. Field of the Invention

The present invention relates to the preparation of anhydrides of carboxylic acids, and more particularly, to an improvement in the production of acetic anhydride by liquid phase carbonylation.

2. Background of the Invention

Acetic anhydride has been known as an industrial chemical for many years and large amounts are used in the manufacture of cellulose acetate. It has long been known that acetic acid and acetic anhydride can be prepared by the carbonylation of methanol and methyl acetate, respectively. Acetic anhydride has commonly been produced on an industrial scale by the reaction of ketene and acetic acid wherein the ketene was generated by high temperature dehydration of acetic acid or the thermal decomposition of acetone. Each of these "classic" processes has well-known drawbacks and disadvantages and the search for an improved process for the production of acetic anhydride has been a continuing one. Proposals for producing anhydrides by the carbonylation reaction of carbon monoxide upon various reactants using cobalt or nickel catalysts under very high pressure is well known. More recently, carbonylation at low pressures has been proposed in processes employing Group VIII noble metal catalysts with and without promoters. This process typically uses a rhodium compound and various promoters to convert a feed stream containing methanol, methyl acetate, dimethyl ether or mixtures thereof, and carbon monoxide to acetic anhydride. For example, U.S. Pat. No. 4,046,807 discloses a method for making acetic anhydride by contacting a noble metal containing catalyst, and preferably rhodium containing catalyst, with carbon monoxide and hydrogen. The '807 patent teaches that the presence of large quantities, that is from 5 to 50 volume %, hydrogen in the reaction gas is very favorable on the carbonylation reaction.

A problem with carrying out carbonylation using such noble metal catalysts and high concentrations of hydrogen is that the acetic anhydride formed is accompanied by ethylidene diacetate (EDA), acetaldehyde and acetic acid. Another problem with using high concentrations of hydrogen in the feed gas is that it increases the formation of methane. To reduce the EDA and methane production, U.S. Pat. No. 4,374,070 teaches liquid phase carbonylation of methyl acetate in the presence of rhodium an iodine compound and lithium wherein from about 2 to 7 volume % of the feed gas is hydrogen. The patent further teaches that the space-time yield is decreased considerably when the amount of hydrogen falls below 2 volume %.

Typically, carbonylation of methyl acetate or methyl ether carried out continuously in the presence of a Group VIII noble metal, with or without the presence of a promoter, further includes a halogen or halide such as methyl iodide to improve the carbonylation process. Volatile components of the reaction mixture are continuously separated from the relatively non-volatile Group VIII noble metal catalyst and the latter is continuously reused for further carbonylation. Typically, although not necessarily, the carbonylation takes place in a carbonylation zone and separation takes place by means of a flash distillation under a pressure lower than that prevailing in the carbonylation zone. Heat can be added or removed or the flash distillation can be carried out adiabatically, as is known to persons skilled in the art. In carrying out such processes where volatile components of the carbonylation mixture are continuously separated from the relatively non-volatile Group VIII noble metal catalyst, and the catalyst reused for further carbonylation, it has been discovered that the Group VIII noble metal catalyst gradually loses its activity and, after prolonged use, may become essentially inactive from a practical standpoint. It is, of course, possible to replace the catalyst at this point but this is an expensive operation even if the deactivated catalyst can be reclaimed.

To overcome this problem U.S. Pat. No. 4,252,741 issued to Porcelli et al. teaches that during the separation of volatile components from the Group VIII noble metal catalyst, a hydrogen partial pressure of at least 10 psi is maintained in a zone in which volatile components of the carbonylation mixture are continuously separated from the Group VIII noble metal. When the carbonylation is carried out in the presence of a metal promoter, such as chromium, it is also preferred to maintain a partial pressure of carbon monoxide of at least 15 psi in the separation zone.

U.S. Pat. No. 4,430,273 issued to Erpenbach et al. teach using a heterocyclic aromatic compound containing quaternary nitrogen and an aliphatic carboxylic acid having 1 to 8 carbon atoms in place of an organonitrogen compound or organophosphorus in a carbonylation process that uses Group VIII metal catalyst, an iodide compound and a promoter such as chromium, iron, cobalt, nickel and an organonitrogen compound or organophosphorus.

U.S. Pat. No. 4,661,631 issued to Becker et al. discloses a process for making acetic acid by the carbonylation of methanol in the presence of a catalyst comprising molybdenum-nickel or tungsten-nickel co-catalyst component in the presence of an iodide and in the presence of a promoter comprising an organo-phosphorus compound or an organo-nitrogen compound. Becker teaches that the rate of carbonylation wherein methanol is converted to acetic acid can be increased by carrying out the carbonylation with a mixture of hydrogen and carbon monoxide where a ratio of their respective partial pressures in the carbonylation zone is maintained at 0.05 to 0.4.

U.S. Pat. No. 4,735,749 issued to Fujiwa et al. disclose a process for maintaining the activity of the Group VIII metal catalyst used in carbonylation process for making an O-acetyl compound, such as acetic anhydride, where methyl acetate is reacted with carbon monoxide using a rhodium catalyst and an iodine compound. The process includes the step of regenerating the rhodium carbonylation catalyst by feeding the non-volatile, rhodium catalyst-containing solution, which is substantially free of any volatile components, into a treatment zone having a partial pressure of hydrogen of at least 0.2 kg/cm$^2$ and heating the catalyst solution at a temperature from 100° C. to 200° C., for about 0.1 to about 2.0 hours. The regenerated catalyst is then re-circulated into the carbonylation reactor.

U.S. Pat. No. 4,994,608 issued to Torrence et al. disclose an improved process for carbonylation of methanol to acetic acid. Aside from the fact that the reaction is different from the one which the present invention is concerned, Torrence teaches converting an alcohol with carbon monoxide in the presence of a reaction medium comprising a rhodium catalyst, the ester of the alcohol being carbonylated with the acid product of the carbonylation reaction, a halide derivative of the hydrocarbon corresponding to the alcohol, especially the halide, and an iodide ion which is present in amount over and above the iodide which is present as the hydrocarbon halide, a water concentration of less than about 14 weight % and where the reaction medium further contains hydrogen in an amount sufficient to provide a hydrogen partial pressure of at least about 4.0 psi in the reactor.

U.S. Pat. No. 5,237,097 issued to Smith et al. discloses a method for solving the problem of rhodium-containing catalysts precipitating from the liquid phase recycle reactants present in a carbonylation process separation vessel. To prevent precipitation of the rhodium from the liquid catalyst, Smith disclose simultaneously adding with the liquid carbonylation product solution at the separation zone a carbon monoxide containing gas stream maintained at a partial pressure of up to about 30 psi.

Japanese patent publication 640998/1994 discloses a process for preparing acetic acid by reacting methanol with carbon monoxide in the presence of a rhodium containing catalyst and a metal iodide in a continuous process having no more than about 10 weight % water. The products are subjected to an evaporation step at a lower pressure than the carbonylation reaction and where the evaporation is carried out at a hydrogen partial pressure of at least 0.1 bar and/or the rhodium containing components are treated with hydrogen and carbon monoxide at a partial pressure of at least 0.1 bar.

It will be recognized that a common disadvantage of the aforementioned processes that treat the liquid phase rhodium-containing catalyst with hydrogen and/or carbon monoxide in a separate vessel where evaporation is simultaneously occurring is that much greater volumes of hydrogen and/or carbon monoxide are required to maintain the requisite partial pressures of the gases. Accordingly, there is still a need for a continuous carbonylation process that utilizes a Group VIII metal catalyst wherein the catalyst maintains its activity over a prolonged period of time without excessive losses of reactant materials.

It is therefore an object of the present invention to provide a further improved process utilizing carbonylation in the presence of a catalyst of the character just described.

SUMMARY OF THE INVENTION

Broadly, this invention is an improvement in the liquid-phase carbonylation of methyl acetate to produce acetic anhydride using Group VIII metal catalyzed reactions. In particular, the invention is directed toward producing acetic anhydride wherein hydrogen, and optionally in combination with carbon monoxide, is contacted with a recycle stream containing recovered Group VIII metal containing catalyst.

In accordance with the present invention, an improved process is provided for preparing acetic anhydride by liquid phase carbonylation of methyl acetate. In the carbonylation process, a feed mixture containing methyl acetate dimethyl ether or a mixture thereof, carbon monoxide, hydrogen, a halogen or halide compound, and optionally lithium are continuously fed to a carbonylation zone and reacted using a Group VIII metal containing catalyst. Such carbonylation processes are well known and are generally described above in the aforementioned patent art. A reaction mixture is continuously removed and fed to a evaporator /separation zone to separate the volatile lower boiling components, such as, methyl iodide, methyl acetate and/or dimethyl ether, acetic acid, acetic anhydride, hydrogen, carbon monoxide from the high boiling components such as a solution of catalyst components in a mixture of acetic acid and acetic anhydride. The catalyst components, which includes the Group VIII metal containing catalyst and co-promoters such as lithium halides, if present, is removed from the evaporator and recycled back to the carbonylation zone. In accordance with one embodiment of the present invention, the recycled Group VIII metal containing catalyst stream is contacted with a hydrogen containing gas stream for a period of from about 0.001 seconds to about 200 seconds as it is being returned to the carbonylation zone.

In another embodiment of the present improvement invention, the recycled Group VIII metal containing catalyst stream is contacted with a gas stream containing a mixture of hydrogen and carbon monoxide for a period of from about 0.001 seconds to about 200 seconds as it is being returned to the carbonylation zone.

In yet another embodiment of the present improvement invention the liquid feed constituents are combined with the recycled Group VIII metal containing catalyst stream to form a consolidated liquid feed stream which is then contacted with a hydrogen gas stream for a period of from about 0.001 seconds to about 200 seconds as it is being returned to the carbonylation zone.

In another embodiment of the present improvement invention the liquid feed constituents are combined with the recycled Group VIII metal containing catalyst stream to form a consolidated liquid feed stream which is then contacted with a gas stream containing a mixture of hydrogen and carbon monoxide for a period of from about 0.001 seconds to about 200 seconds as it is being returned to said carbonylation zone.

It has been unexpectedly discovered that by contacting the recycled Group VIII metal containing with a gas stream containing hydrogen for a period of from about 0.001 seconds to about 200 seconds prior to entering the carbonylation zone, the catalyst maintains its activity essentially indefinitely and the total amount of hydrogen in the carbonylation zone can be less than 2 volume %, based on total amount of carbon monoxide and hydrogen fed to the carbonylation zone. Such results are quite surprising given the state of the prior art which utilized significantly greater quantities of hydrogen for maintaining catalytic activity, whether introduced in the separation zone or in the carbonylation zone.

A further advantage of process of the present invention is that the reduced hydrogen content in the carbonylation zone effectively and significantly reduces the amount of side products produced, such as ethylidene diacetate (EDA).

It is another object of the present invention to provide a continuous liquid-phase process for producing acetic anhydride involving the carbonylation of methyl acetate wherein the activity of the Group VIII metal containing catalyst is maintained even during prolonged carbonylation operations.

It is another object of the invention to provide a process where the introduction of hydrogen into the carbonylation zone is minimized whereby side reactions and the production of EDA is reduced.

DETAILED DESCRIPTION OF THE INVENTION

The following description is directed to the carbonylation of methyl acetate to produce acetic anhydride using a number of techniques which are well known and have been partially described in the above patent references cited as well as the literature cited therein. However, one will understand that the process of the present invention is not so limited and is applicable to the carbonylation of methanol to form acetic acid and its homologues.

The present invention involves an improvement in the carbonylation of an alcohol, an acid, an ester or an ether, but is herein described with reference to the carbonylation of an ester and more particularly, methyl acetate. Specifically, the improved process is directed at an improved overall system productivity by maintaining an optimal carbonylation catalytic activity and reducing the production of hydrogen promoted side reactions such as the production of EDA.

Generally, the liquid-phase carbonylation of methyl acetate for production of acetic anhydride is carried out by intimately contacting a stream of liquid reactants, such as methyl acetate and methanol with gaseous carbon monoxide which is bubbled through a liquid reaction medium containing a Group VIII metal-containing catalyst, a promoting component and preferably a halogen-containing promoting component and an additional soluble iodide salt promoter at conditions of temperature and pressure suitable to form the carbonylation product. An important addition to the reaction medium is a finite concentration of hydrogen. It will, of course, be understood that methyl acetate can be replaced or supplemented with dimethyl ether in the feed. It has been observed that the dimethyl ether is converted to methyl acetate in the carbonylation reaction so that it may be considered a methyl acetate precursor. Carbonylation takes place in a carbonylation zone where the liquid and gaseous reactants, the liquid-phase Group VIII metal-containing catalyst, and any promoters are intermixed and react to form a liquid reaction product. It is to be understood that the carbonylation zone can be comprised of a single reaction zone or a plurality of zones such as those described in U.S. Pat. No. 5,922,911, the disclosure of which is incorporated herein by reference.

The liquid carbonylation reaction product solution formed in the reaction zone is subsequently conveyed to an evaporation or separation zone where low boiling products and unreacted vaporous constituents are flashed off. Typically, this zone has a lower pressure compared to that of the reaction zone. In the process of the present invention, a homogeneous catalytic agent, present in the liquid carbonylation product solution, remains in solution and is recycled back into the reaction zone, along with the portion of the liquid carbonylation product solution which was not flashed off in the separation zone. As is known in the art, but unrelated to the present improvement, the flashed off product is transferred to a purification zone to separate the desired carbonylation product from undesired side products.

Carbonylation of methyl acetate with carbon monoxide is facilitated by the use of a catalyst, most suitably a Group VIII noble metal, such as, rhodium, iridium, ruthenium, palladium, osmium and/or platinum, as disclosed in U.S. Pat. No. 4,115,444. Carbonylation is typically carried out at temperatures, that is, the temperature in the carbonylation reaction zone, of between about 50° C. to about 500° C. Preferably, the temperature in the carbonylation reaction zone is between about 75° C. to about 275° C. More preferably, the temperature in the reaction zone is in the range of about 160° C. to about 200° C. The reaction zone is further under a pressure of between about 15 psia to about 2000 psia. Preferably, the pressure in the reaction zone is in the range of between about 50 psia and about 1200 psia, more preferably, between about 100 psia and about 1000 psia and still more preferably, between about 500 psia and about 900 psia.

The Group VIII noble metal carbonylation catalyst can be supplied and used in any convenient form, such as, in the zero valent state or in any higher valent form. Non-limiting examples of suitable catalytic species include, the metal itself in finely-divided form, or as a metal carbonate, oxide, hydroxide, bromide, iodide, chloride, lower alkoxide (methoxide), phenoxide or metal carboxylate wherein the carboxylate ion is derived from an alkanoic acid of 1 to 20 carbon atoms. Complexes of the metals may also be employed, e.g. the metal carbonyls, such as iridium and rhodium carbonyls, e.g. hexarhodium hexadecacarbonyl, or as other complexes such as the carbonyl halides, or acetylacetonates, e.g. rhodium acetylacetonate. The most preferred Group VIII metal is rhodium, such catalytic agents as rhodium metal, rhodium oxide, an organorhodium compound, a rhodium carbonyl complex, a rhodium carbonyl halide, rhodium nitrate and rhodium halides, i.e., rhodium chloride, rhodium bromide and rhodium iodide are particularly preferred catalytic agents in this carbonylation process. Of these carbonylation catalysts, rhodium metal, rhodium oxide, a rhodium halide and a rhodium carbonyl complex are even more particularly preferred. Of the rhodium halides, rhodium iodide and rhodium chloride are the most preferred. The metal employed may contain impurities normally associated with the commercially available metal or metal compounds, and need not be purified any further. Thus, the commercially available metal or metal compound is suitably employed.

The amount of Group VIII noble metal catalyst is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, the catalyst is employed in the amount of 1 mole per 10 to 100,000 moles of ester, preferably 1 mole per 50 to 10,000 moles of ester, and most preferably 1 mole per 50 to 3,000 moles of ester.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired carbon monoxide partial pressure. The carbon monoxide, like the other reactants, should, however, be essentially dry, i.e., the carbon monoxide and the other reactants should be reasonably free from water. The presence of minor amounts of water such as may be found in the commercial forms of the reactants is, however, acceptable.

It has been previously found that the activity of the Group VIII metal containing catalyst described above can be improved, particularly with respect to the reaction rate and product concentration by the concurrent use of hydrogen and a promoting component. Hydrogen not only suppresses the formation of tar but significantly increases the reaction rate in both the methyl acetate conversion and the acetic anhydride production. In accordance with the present invention, it was unexpectedly discovered that the amount of hydrogen fed to the carbonylation zone can be less than 2 volume % and preferably is from about 0.01 to about 1.8 volume %, more preferably from about 0.5 to about 1.5 volume %, and most preferably from about 1.1 to about 1.4 volume % based on the total amount of hydrogen and carbon monoxide fed to the carbonylation zone. It was further unexpectedly discovered that even as such low concentrations of hydrogen it was possible to maintain good space-time yields of acetic anhydride while advantageously reducing the amount of EDA produced by greater than about 25%. Preferably, the EDA produced is reduced by greater than about 35% and more preferably the EDA produced is reduced by greater than about 60%. As expressed herein the reduction of EDA produced is representative of the amount of EDA produced if the hydrogen is introduced into the carbonylation zone only, relative to the amount of EDA produced when hydrogen is introduced into the carbonylation zone in accordance with the embodiments of the present invention.

Effective promoters include the elements having atomic weights greater than 5 of groups IA, IIA, IIIA, IVB, VIB, the non-noble metals of Group VIII and the metals of the lanthanide and actinide groups of the Periodic Table. Particularly preferred are the lower atomic weight metals of each of these groups, e.g. those having atomic weights lower than 100, and especially preferred are metals of groups IA, IIA and IIIA as are metals of group VIB and the non-noble metals of Group VIII. In general, the most suitable elements are lithium, magnesium, calcium, titanium, chromium, iron, nickel and aluminum. Particularly preferred elements are lithium and chromium. The promoters may be used in their elemental form, e.g. as finely-divided or powdered metals, or they may be employed as compounds of various types, both organic and inorganic, which are effective to introduce the element into the reaction system. Thus, typical compounds of the promoter elements include oxides, hydroxides, halides, e.g. bromides and iodides, oxyhalides, hydrides, alkoxides, and the like. Especially preferred organic compounds are the salts of organic mono-carboxylic acids, e.g. alkanoates such as acetates, butyrates, decanoates and laurates, benzoates, and the like. Other compounds include the metal alkyls, carbonyl compounds as well as chelates, association compounds and enol salts. Particularly preferred are the elemental forms, compounds which are bromides or iodides, and organic salts, e.g. salts of the mono-carboxylic acid corresponding to the anhydride being produced. Desirably, the halogen or halide is selected from $I_2$, $Br_2$, $Cl_2$, hydrogen iodide, hydrogen bromide, hydrogen chloride, methyl iodide, methyl bromide, methyl chloride, ethyl iodide, ethyl bromide, ethyl chloride and mixtures thereof. Preferably, the halide promoter is present in the form of an alkyl halide in which the alkyl radical corresponds to the alkyl radical of the feed alcohol which is carbonylated. For example, in the carbonylation of methanol to acetic acid, the halide promoter will comprise methyl halide, and more preferably methyl iodide. If desired, mixtures of promoters may also be used, especially mixtures of elements from different groups of the Periodic Table.

More particularly, the promoter may be (1) an inorganic iodide salt such as lithium iodide or an iodide salt of a quaternary organophosphorus or organonitrogen compound or (2) an inorganic compound or an organophosphorus or organonitrogen compound which forms an iodide salt in the carbonylation zone. The organophosphorus or organonitrogen iodides may be selected from phosphonium iodides, ammonium iodides and heterocyclic aromatic compounds in which at least one ring hetero atom is a quaternary nitrogen atom. Examples of such phosphorus- and nitrogen-containing iodides include tetra(hydrocarbyl)phosphonium iodides such as tributyl(methyl)phosphonium iodide, tetrabutylphosphonium iodide, tetra-octylphosphonium iodide, triphenyl(methyl)phosphonium iodide, tetraphenylphosphonium iodide and the like; tetra(hydrocarbyl)ammonium iodides such as tetrabutylammonium iodide and tributyl (methyl)ammonium iodide; and heterocyclic aromatic compounds such as N-methylpyridinium iodide, N,N'-dimethylimidazolium iodide, N-methyl-3-picolinium iodide, N-methyl-2,4-litidinium iodide, N-methyl-2,4-lutidinium iodide and N-methylquinolinium iodide. The preferred iodide salt promoters comprise lithium iodide and tetraalkylphosphonium iodides, triphenyl(alkyl) phosphonium iodides, tetraalkylammonium iodides and N,N'-dialkylimidazolium iodides wherein the alkyl groups contain up to about 8 carbon atoms.

A portion or all of the promoter compound may be fed as a compound which forms an iodide salt in the carbonylation zone. Thus, the promoter compounds may be fed initially in the form of their corresponding acetates, hydroxides, chlorides or bromides or the phosphorus- and nitrogen-containing promoters may be fed as compounds in which the phosphorus or nitrogen atoms are trivalent, e.g., tributylphosphine, tributylamine, pyridine, imidazole, N-methylimidazole and the like, which are quaternized by the methyl iodide present in the carbonylation zone.

The amount of the iodide salt promoter present in the carbonylation zone can be varied substantially depending on a variety of factors, especially on the particular promoter used. Preferably, the promoter is used in the amount of 0.0001 mole to 100 moles per mole of Group VIII noble metal catalyst, most preferably 0.001 to 50 moles per mole of catalyst. For example, the concentration of lithium iodide in the reaction mixture may range from about 175 to 5000 ppm Li, preferably about 1500 to 3700 ppm Li, whereas the phosphorus- and nitrogen-containing promoters may be present in concentrations of about 0.5 to 25 weight percent, calculated as their iodide salts and based on the total weight of the reaction mixture, i.e., the contents of the carbonylation zone. The amounts of other materials, e.g., acetic acid, acetic anhydride, methyl iodide, methyl acetate and/or dimethyl ether present in the reaction mixture vary substantially depending, for example, on the carbonylation rate, residence time and concentrations of the iodide salt promoter and acetic acid solvent.

In the working up of the reaction mixtures, e.g. by distillation, as discussed above, the promoter generally remains with the Group VIII metal catalyst, i.e. as one of the least volatile components, and is suitably recycled or otherwise handled along with the catalyst.

The step of separating a liquid carbonylation product formed in the carbonylation reaction step into a volatile component stream and a non-volatile stream having the Group VIII metal-containing catalyst solution can be practiced by using well-known techniques such as flash distillation. In this step, most of the low-boiling compounds such as the methyl iodide, methyl acetate and/or dimethyl ether, acetic acid, acetic anhydride, hydrogen, carbon monoxide are distilled off to subsequent recovery processes known in the art. Suitably, the conditions maintained in the separation zone are substantially lower than the conditions of the carbonylation zone and comprises a total pressure, including that provided by the partial pressure of the carbon monoxide, in the range of between about 15 psia to about 60 psia, desirably, from about 15 psia to about 45 psia, preferably, from about 20 psia to about 40 psia and more preferably, from about 20 psia to about 30 psia. The temperature in the separation zone can be from about 100° C. to about 200° C. Preferably, the temperature is from about 120° C. to about 180° C. More preferably, the temperature in the separation zone is from about 140° C. to about 160° C.

The recovered Group VIII metal-containing catalyst is recycled back to the carbonylation zone for further use. In accordance with the present invention, the recycled Group VIII metal-containing catalyst is contacted with a hydrogen containing stream wherein the amount of hydrogen contacting the recovered Group VIII metal-containing catalyst is from about 0.01 to 1.8 volume %, preferably from about 0.5 to 1.5 volume % and more preferably from 1.1 to 1.4 volume %, wherein the volume % is based on the total amount of hydrogen and carbon monoxide fed to the carbonylation zone. The hydrogen in the gas stream should contact the Group VIII metal-containing catalyst before entering the carbonylation zone for a period ranging from about 0.001 seconds to about 200 seconds, preferably from about 0.1 seconds to about 10 second and more preferably from about 0.1 seconds to about 5 seconds. As discussed above, the reaction medium includes a finite amount of hydrogen in the carbonylation zone. In feeding the prescribed amount of hydrogen to the carbonylation zone, from about 1% to 100% can be provided by the gas stream contacting the Group VIII metal-containing catalyst, and preferably, from about 20% to about 95% of the hydrogen in the carbonylation zone is provided by the gas stream contacting the Group VIII metal-containing catalyst.

In accordance with another aspect of the present improvement, the gas stream contacting the Group VIII metal-containing catalyst includes carbon monoxide. The gas stream contacts the Group VIII metal-containing catalyst for a period of from about 0.001 seconds to about 200 seconds as it is being returned to the carbonylation zone. The volumetric ratio of carbon monoxide to hydrogen in the gas stream can range from about 0.01 to about 2.0 with preferred ranges being from about 0.1 to about 1.0.

In another embodiment of the present invention, the liquid feed constituents to the carbonylation zone are combined with the recycled Group VIII metal containing catalyst stream to form a consolidated feed liquid feed stream. The consolidated feed stream is contacted with a hydrogen gas stream as described above for a period of from about 0.001 seconds to about 200 seconds as it is being returned to the carbonylation zone.

In yet another embodiment of the present invention, the liquid feed constituents to the carbonylation zone are combined with the recycled Group VIII metal containing catalyst stream to form a consolidated feed liquid feed stream as described above. The consolidated feed stream is contacted with a gas stream containing a mixture of hydrogen and carbon monoxide for a period of from about 0.001 seconds to about 200 seconds as it is being returned to said carbonylation zone.

The following examples are for illustration purposes only and serve to provide a better understanding of the invention and as such are not to be construed as limiting the invention to what is disclosed therein.

COMPARATIVE EXAMPLE A

A reaction mixture comprising liquid constituents methyl acetate, acetic acid, methyl iodide, acetic anhydride, and Group VIII metal-containing catalyst components is continuously fed to a commercial scale reactor system consisting of one or more baffled, back-mixed reaction vessels. Carbon monoxide gas, containing 1.8% hydrogen is contacted in the reaction vessel with the reaction mixture by means of a gas sparging device, to produce acetic anhydride. By-product EDA is formed at a rate of 0.0065 lb EDA/lb acetic anhydride.

EXAMPLE 1

The procedure of Comparative Example A was repeated except that the liquid constituents, including the Group VIII metal-containing catalyst were contacted with a gas stream containing a portion of the hydrogen and carbon monoxide fed to the carbonylation zone. Total carbon monoxide feed to the carbonylation zone was reduced by 0.5 volume % and the total amount of hydrogen fed to the carbonylation zone was 1.2 volume %, based on the total amount of carbon monoxide and hydrogen fed to the carbonylation zone. At these conditions, reactor productivity remains unchanged, and the EDA formation rate drops to 0.0044 lb EDA/lb acetic anhydride.

EXAMPLE 2

The procedure of Comparative Example A was repeated except that the liquid constituents, including the Group VIII metal-containing catalyst were contacted with a gas stream containing approximately 0.8 volume % hydrogen and a portion of the carbon monoxide fed to the carbonylation zone. The total amount of hydrogen fed to the carbonylation zone is about 0.9 volume %. At these conditions, reactor productivity decreases 10%, and remains constant at this level though extended recycling of the catalyst. The EDA formation rate drops to 0.0038 lb EDA/lb acetic anhydride.

Although the present invention has been described in terms of the presently preferred embodiment, it is to be understood that such disclosure is not to be interpreted as limiting to the invention described herein. No doubt that after reading the disclosure, various alterations and modifications will become apparent to those skilled in the art to which the invention pertains. It is intended that the appended claims be interpreted as covering all such alterations and modifications as fall within the spirit and scope of the invention.

What is claimed is:

1. In a liquid phase carbonylation process for the production of acetic anhydride by reacting in a carbonylation zone a feed stream comprising methyl acetate, dimethyl ether or mixtures thereof, methanol, carbon monoxide and hydrogen using a Group VIII metal-containing catalyst and a halogen or halide containing material, wherein a liquid reaction product is continuously withdrawn from the carbonylation zone and fed to an evaporation/separation zone to separate volatile constituents of the reaction from the non-volatile constituents prior to returning the non-volatile constituents to the carbonylation zone, wherein the non-volatile constituents includes a portion of the Group VIII metal catalyst from the carbonylation reactor having a reduced catalytic activity, wherein the improvement for regenerating said Group VIII metal-containing catalyst and reducing an amount of EDA produced comprises contacting said Group VIII metal-containing catalyst with a gas stream having from 0.01 to 1.8 volume % hydrogen for a period of from about 0.001 seconds to about 200 seconds as said Group VIII metal-containing catalyst is being returned to said carbonylation zone whereby a hydrogen treated Group VIII metal-containing catalyst is obtained and re-circulated to said carbonylation zone.

2. The process of claim 1 wherein said Group VIII metal is rhodium.

3. The process of claim 2 wherein said separation zone is maintained at a pressure of from about 20 psi to about 60 psi and a temperature of from about 100° C. to about 200° C.

4. The process of claim 1 wherein said Group VIII metal is selected from the group consisting of rhodium metal, rhodium oxide, an organorhodium compound, a rhodium carbonyl complex, a rhodium carbonyl halide, rhodium nitrate, rhodium halide and mixtures thereof.

5. The process of claim 1 wherein said halogen or halide is selected from the group consisting of $I_2$, $Br_2$, $Cl_2$, hydrogen iodide, hydrogen bromide, hydrogen chloride, methyl iodide, methyl bromide, methyl chloride, ethyl iodide, ethyl bromide, ethyl chloride and mixtures thereof.

6. The process of claim 1 wherein said gas stream includes carbon monoxide at a partial pressure of from about 0.001 psi to about 1000 psi.

7. The process of claim 6 wherein said gas stream has a volumetric ratio of $CO/H_2$ of from 0.1 to 2.0.

8. The process of claim 1 wherein from about 0.5 to about 1.5 volume % hydrogen is present in said carbonylation zone and wherein from about 1% to about 100% of said hydrogen is fed by said gas stream.

9. The process of claim 1 wherein said gas stream has a contact time of from about 0.1 seconds to about 10 seconds.

10. The process of claim 1 wherein said gas stream has a contact time is from about 0.1 seconds to about 5 seconds.

11. The process of claim 8 wherein from about 1.1 to about 1.4 volume % hydrogen is present in said carbonylation zone and wherein from about 20% to about 95% of said hydrogen is fed by said gas stream.

12. The process of claim 1 wherein the amount of EDA produced is reduced by greater than about 25%.

13. The process of claim 1 wherein the amount of EDA produced is reduced by greater than about 35%.

14. The process of claim 1 wherein the amount of EDA produced is reduced by greater than about 60%.

15. In a liquid phase carbonylation process for the production of acetic anhydride by reacting in a carbonylation zone a feed stream having liquid constituents comprising methyl acetate, dimethyl ether or mixtures thereof, methanol, and vaporous constituents comprising carbon monoxide and hydrogen, using a rhodium containing catalyst and a halogen or halide containing material, wherein a liquid reaction product is continuously withdrawn from the carbonylation zone and fed to an evaporation/separation zone to separate volatile constituents of the reaction from the non-volatile constituents prior to returning the non-volatile constituents to the carbonylation zone, wherein the non-volatile constituents includes a portion of the rhodium-containing catalyst from the carbonylation reactor having a reduced catalytic activity, wherein the improvement for regenerating said rhodium-containing catalyst and reducing an amount of EDA produced by greater than about 25% comprises combining said liquid feed constituents with said recycled Group VIII metal containing catalyst stream to form a consolidated liquid feed stream and contacting said consolidated liquid feed stream with a gas stream having from 0.01 to 1.8 volume % hydrogen for a period of from about 0.001 seconds to about 200 seconds whereby a hydrogen treated Group VIII metal-containing catalyst is obtained and re-circulated to said carbonylation zone.

16. The process of claim 15 wherein said rhodium-containing material is selected from the group consisting of rhodium metal, rhodium oxide, an organorhodium compound, a rhodium carbonyl complex, a rhodium carbonyl halide, rhodium nitrate, rhodium halide and mixtures thereof.

17. The process of claim 15 wherein said halogen or halide is selected from the group consisting of $I_2$, $Br_2$, $Cl_2$, hydrogen iodide, hydrogen bromide, hydrogen chloride, methyl iodide, methyl bromide, methyl chloride, ethyl iodide, ethyl bromide, ethyl chloride and mixtures thereof.

18. The process of claim 15 wherein said gas stream includes carbon monoxide at a partial pressure of from about 0.001 psi to about 1000 psi and said gas stream has a volumetric ratio of $CO/H_2$ of from 0.1 to 2.0.

19. The process of claim 15 wherein from about 0.5 to about 1.5 volume % hydrogen is present in said carbonylation zone and wherein from about 1% to about 100% of said hydrogen is fed by said gas stream.

20. The process of claim 15 wherein said gas stream has a contact time of from about 0.1 seconds to about 10 seconds.

21. The process of claim 15 wherein from about 1.1 to about 1.4 volume % hydrogen is present in said carbonylation zone, from about 20% to about 95% of said hydrogen is fed by said gas stream and wherein said gas stream has a contact time of from about 0.1 seconds to about 5 seconds.

22. The process of claim 15 wherein the amount of EDA produced is reduced by greater than about 35%.

23. The process of claim 15 wherein the amount of EDA produced is reduced by greater than about 60%.

* * * * *